United States Patent [19]

Versiani et al.

[11] Patent Number: 5,371,082
[45] Date of Patent: Dec. 6, 1994

[54] TREATMENT OF ANXIETY DISORDERS

[76] Inventors: Marcio Versiani, Avda. Copacabana 1133, S. 1303, BR-22070 Rio de Janeiro, Brazil; Roman Amrein, 31 Landhausweg, CH-4126 Bettingen, Switzerland

[21] Appl. No.: 121,005

[22] Filed: Sep. 14, 1993

Related U.S. Application Data

[63] Continuation of Ser. No. 936,709, Aug. 27, 1992, abandoned, which is a continuation of Ser. No. 807,972, Dec. 16, 1991, abandoned, which is a continuation of Ser. No. 692,873, Apr. 29, 1991, abandoned.

[30] Foreign Application Priority Data

Nov. 29, 1990 [EP] European Pat. Off. ........ 90122789.2

[51] Int. Cl.$^5$ ............................................. A61K 31/535
[52] U.S. Cl. ................................................... 514/237.8
[58] Field of Search ................ 514/237.8, 238.8, 239.5

[56] References Cited

U.S. PATENT DOCUMENTS

| | | | |
|---|---|---|---|
| 4,210,754 | 7/1980 | Burkard et al. | 544/167 |
| 4,906,626 | 8/1990 | Amrein et al. | 514/237.8 |

OTHER PUBLICATIONS

Dowson, J. H., J. Neural Transm. Suppl., vol. 23, 1987, pp. 121–138.
Bechelli et al., Curr. Med. Res. Opin., vol. 11/suppl. 1, 1989, pp. 38–52.
Da Prada, et al., J. Pharmacol. Exp. Ther., 248:400–414 (1989).
Schoerlin, et al., Acta. Psychiatr. Scan. Suppl. 82(630):108–110 (1990).
Liebowitz, et al., *Journal of Clinical Psychopharmacology*, 6:2 pp. 93–98 (1986).
Noyes, et al., *J. Clin. Psychiatry.*, vol. 51, pp. 24–30 (1990).
Liebowitz, et al., *Acta Psychiatr. Scand.*, Suppl., vol. 82(360), pp. 29–34 (1990).
Liebowitz, et al., *Psychiatry Research*, 22:89–90 (1987).

*Primary Examiner*—Marianne M. Cintins
*Assistant Examiner*—Kimberly R. Jordan
*Attorney, Agent, or Firm*—George M. Gould; George W. Johnston; John P. Parise

[57] ABSTRACT

The invention relates to the use of p-chloro-N-(2-morpholinoethyl)benzamide in the treatment of anxiety disorders, such as, panic disorders, social phobia and obsessive compulsive disorder,

5 Claims, 2 Drawing Sheets

TREATMENT OF ANXIETY DISORDERS

This is a continuation of application Ser. No. 07/936,709 filed Aug. 27, 1992, now abandoned, which is a continuation of 07/807,972 filed Dec. 16, 1991, now abandoned, which is a continuation of Ser. No. 07/692,873 filed Apr. 29, 1991, now abandoned.

BRIEF SUMMARY OF THE INVENTION

The invention relates to the use of p-chloro-N-(2-morpholinoethyl)benzamide [also known as moclobemide] in the treatment of anxiety disorders, such as, panic disorders, social phobia and obsessive disorders.

BACKGROUND OF THE INVENTION

Depressive and anxiety symptoms frequently overlap. Efficacy of tricyclic antidepressants (TCAs) and classical irreversible monoamine oxidase inhibitors (MAOIs) in anxiety disorders has been demonstrated in results from clinical trials and case reports. The anxiolytic effects of antidepressants are widely believed to be specific and not an epiphenomenon of antidepressant or patholytic effects. In long term treatment, tricyclic antidepressants (TCAs) appear to be effective. However, the poor tolerance of TCAs and the risks associated with conventional irreversible MAOIs are limitations to their usefulness.

Therefore, there is a strong demand for alternative drugs particularly for chronic and long term treatment.

As defined in the DSM III-R (Diagnostic and Statistical Manual of Mental Disorders [Third Edition-Revised], American Psychiatric Association, Washington DC, 1987), anxiety disorders comprise—among others—panic disorder with or without agoraphobia, social phobia, and obsessive compulsive disorder.

Panic disorder is classified as an anxiety disorder because in panic disorder, anxiety is usually the predominant symptom. Panic attacks are defined as discrete episodes of intense fear or apprehension, of sudden onset and not associated with physical exertion. Avoidance behavior is almost always present in panic disorder with agoraphobia.

In the natural course of panic disorder with agoraphobia, spontaneous panic attacks almost always precede the phobic symptoms with most patients developing disabling phobic symptoms within six months after the first onset of spontaneou, unexplained anxiety attack.

The development of severe phobic symptoms coincides with an escalation in the intensity and frequency of the spontaneous panic attacks beyond a tolerable threshold for the patient. When a spontaneous panic attack occurs repeatedly in a specific situation, for example, crowds, a phobic anxiety reaction becomes conditioned to that situation. The disorder generalizes and the disability becomes more severe. The development of phobic symptoms is a function of the frequency and intensity of the spontaneous panic attacks and the situations in which they occur. A phobic disability is conditioned more rapidly in those overwhelming, devastating and frequency spontaneous panic attacks. Once the patient is so conditioned, the phobic anxiety response often persists after the spontaneous panic attacks ends although in the first few years, the phobic disorder is less prominent than the anxiety, hysterical and hypochondriacal symptoms.

Panic disorder is common and disabling. Epidemiological data indicate that the life-time prevalence rate for panic disorder is 1–2%. According to the DSM-III-R, panic disorder is the most common of the anxiety disorders in patients seeking treatment.

Social phobia is classified as an anxiety disorder according to the DSM-III-R since exposure to the specific phobic stimulus almost invariably provokes an immediate anxiety response. Marked anticipatory anxiety occurs if the person is confronted with the necessity of entering into the social phobic situation and such situations are thus usually avoided.

The essential feature of social phobia, according to DSM-III-R, is the persistent fear of one or more situations in which a person is exposed to possible scrutiny by others and fears that he or she may do something or act in a way that will be humiliating or embarrassing. Epidemiological data suggest that approximately 2% of the adult U.S. population meet criteria for social phobia.

In their feared situation, or in anticipation of it, affected individuals can suffer enormous anxiety, as well as sweating, trembling, racing or pounding heart beat, mental confusion, and a desire to flee. Vocational advancement or even work itself may be avoided because of social phobia. Social avoidance and isolation can also become extreme, especially in the more generalized condition. Alcohol abuse is more commonly associated with social phobia than any other anxiety disorder, and frequently represents an attempt at self medication of social fears.

According to DSM III-R, the essential feature of obsessive compulsive disorder is recurrent obsessions, i.e., persistent ideas experienced as intrusive and senseless, or compulsions, i.e., repetitive intentional behavior performed in response to an obsession, that cause distress or interfer with routine activities of the patient.

DETAILED DESCRIPTION OF THE INVENTION

It has now been found that the compound, p-chloro-N-(2-morpholinoethyl)benzamide (moclobemide), is effective in treating anxiety disorders, such as, panic disorders, social phobia and obsessive compulsive disorder.

Accordingly, the invention is concerned with a method of treating a host suffering from anxiety disorders comprising administering to the host moclobemide in an amount effective for treating the anxiety disorder. Furthermore, the invention is concerned with the use of moclobemide in the preparation of pharmaceutical compositions for the treatment of anxiety disorders, such as, panic disorder, social phobia and obsessive compulsive disorder, and with pharmaceutical compositions containing moclobemide in dosage unit form for the treatment of anxiety disorders.

Moclobemide, its preparation and its use as an antidepressant is known, for example, from U.S. Pat. No. 4,210,754. Furthermore, moclobemide is known to be useful in the treatment of cognitive disorders, see U.S. Pat. No. 4,906,626.

The efficacy of moclobemide in the treatment of anxiety disorders can be demonstrated in a double-blind, randomized study in Out-Patients with social phobia (as defined in DSM III-R).

Figure 1:
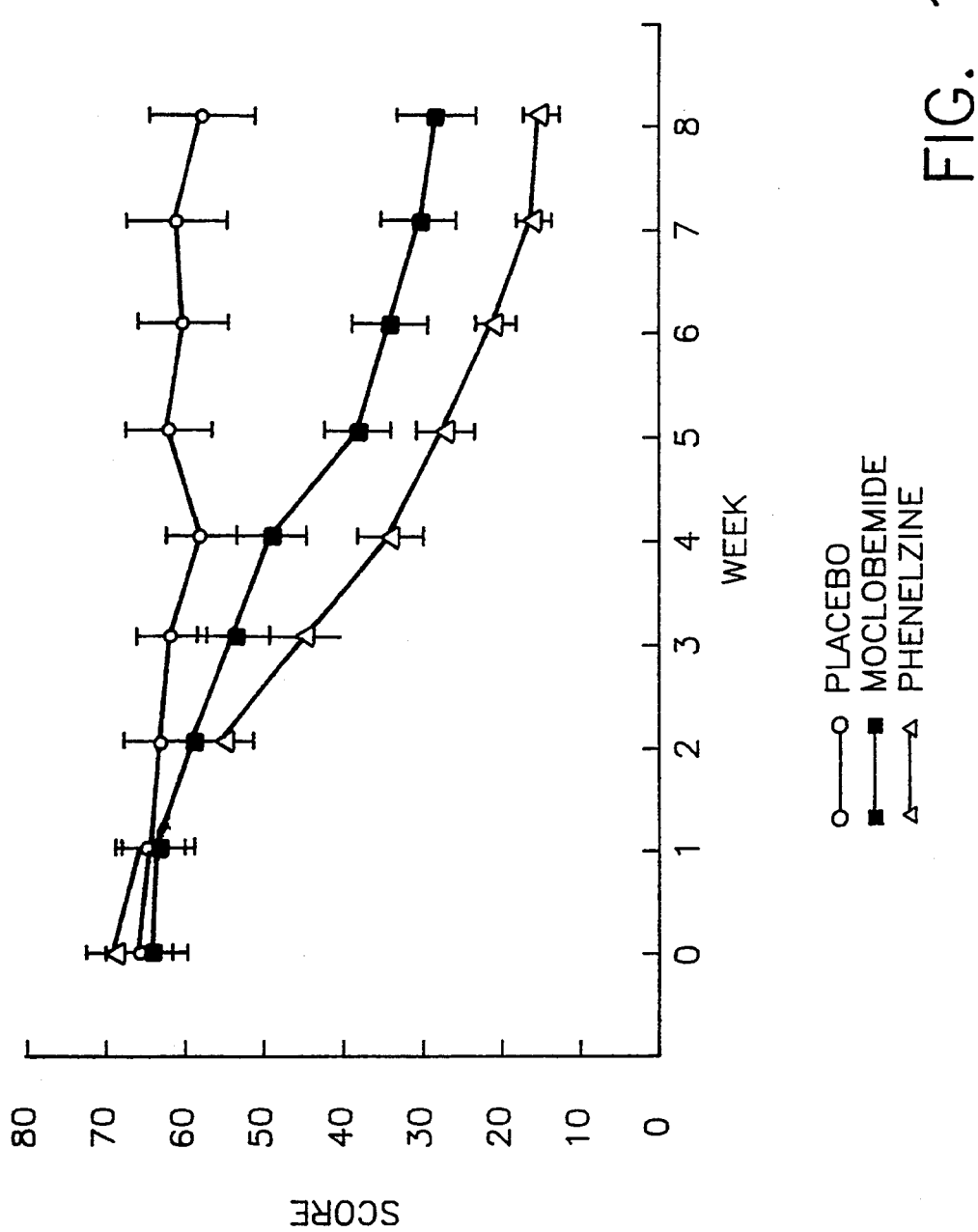
FIG. 1—Graph showing a comparison of Social Phobia Scale score verses time for placebo, moclobemide and phenelzine.
Figure 2:
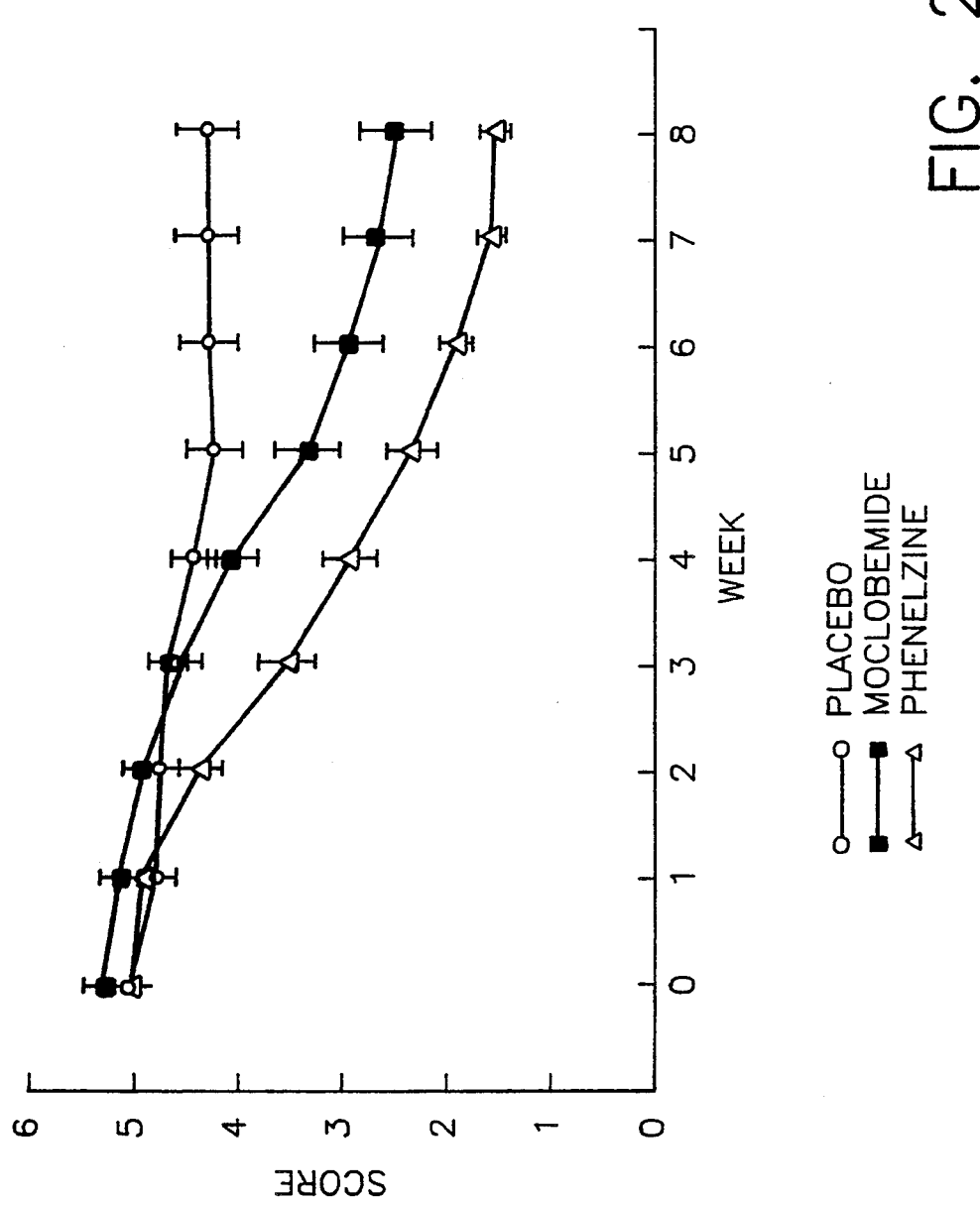
FIG. 2—Graph showing a comparison of Clinical Global Impression severity verses time for placebo, moclobemide and phenelzine.

78 patients of both sexes aged 19-60 years entered the study and received either moclobemide, phenelzine (an irreversible mono amino oxidase inhibitor) or placebo orally for a 24 week period. The target doses were moclobemide=600 mg/day; phenelzine=90 mg/day; placebo=6 capsules/days. Medication was provided in capsules containing either 100 mg of moclobemide, 15 mg of phenelzine or placebo. Patients were rated, inter alia, for social phobia using the Social Phobia Scale (J. Clin. Psychiatry 49: 252–257) and Clinical Global Impressions (CGI). Results are shown in FIGS. 1 and 2. As can be seen therefrom, after 8 weeks treatment both active drugs were clearly more effective than placebo in decreasing social phobia. Moclobemide was, however, much better tolerated than phenelzine. The total number of withdrawals for reasons of side effects was: placebo=0; moclobemide=0; phenelzine=6.

In accordance with the present invention, moclobemide can be administered in conventional pharmaceutical formulations as disclosed, for example, in U.S. Pat. Nos. 4,210,754 and 4,906,626. Preferred are formulations for oral administration such as tablets and capsules containing, for example, 100 or 150 mg or 200 mg moclobemide per dosage unit. Dosages required for the treatment of anxiety disorders with moclobemide may vary with the route of administration, the age, weight and condition of the individual. Typically, the daily dosage for a human adult may vary between 100 and 600 mg p.o. although higher dosages may be administered, if required. The daily dosage is preferably distributed in 2–3 individual doses over the day.

We claim:

1. A method of treating a patient suffering from an anxiety disorder comprising orally administering to the patient requiring such treatment moclobemide in an amount effective to treat the anxiety disorder.

2. The method of claim 1, wherein the anxiety disorder is panic disorder, social phobia or obsessive compulsive disorder.

3. The method of claim 2, wherein moclobemide is administered in unit dosage form.

4. The method of claim 3, wherein the unit dosage form is a tablet or capsule.

5. The method of claim 3, wherein the unit dosage form is a capsule containing 100–200 mg of moclobemide.

* * * * *